United States Patent [19]

Nickell et al.

[11] Patent Number: 4,629,497
[45] Date of Patent: Dec. 16, 1986

[54] CERTAIN 1-(N-METHYLSULFONAMIDO)-PROP-2-YL 2-/4-(PYRID-2-YLOXY)PHENOXY/-PROPIONATE DERIVATIVES AND THEIR USE FOR INCREASING RECOVERABLE SUGAR CONTAINED IN SUGAR CANE

[75] Inventors: Louis G. Nickell, Chicago; Leonard J. Stach, Riverside; Takeo Hokama, Chicago, all of Ill.

[73] Assignee: Sandoz Ltd., Basel, Switzerland

[21] Appl. No.: 766,731

[22] Filed: Aug. 19, 1985

[51] Int. Cl.$^4$ .................... C07D 213/64; A01N 43/40
[52] U.S. Cl. ........................................ 71/94; 546/294; 546/302
[58] Field of Search ............................ 546/294; 71/94

[56] References Cited

U.S. PATENT DOCUMENTS 4,556,413 12/1985 Frater et al. ............................ 71/94

Primary Examiner—Alan L. Rotman
Attorney, Agent, or Firm—Gerald D. Sharkin; Richard E. Vila

[57] ABSTRACT

The subject matter of this invention are the following sulfonamides:

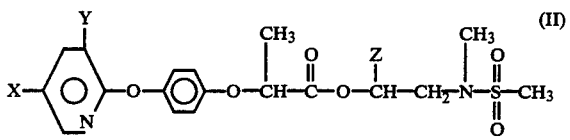

wherein
X is chlorine or trifluoromethyl
Y is chlorine or hydrogen
Z is hydrogen or methyl 16 Claims, No Drawings

CERTAIN 1-(N-METHYLSULFONAMIDO)-PROP-2-YL 2-/4-(PYRID-2-YLOXY)PHENOXY/-PROPIONATE DERIVATIVES AND THEIR USE FOR INCREASING RECOVERABLE SUGAR CONTAINED IN SUGAR CANE

This invention relates to new sulfonamide esters of the following structural formula:

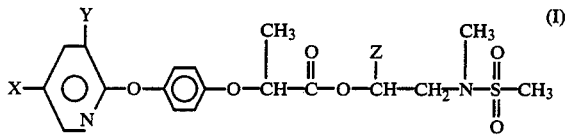

wherein
X is chlorine or trifluoromethyl
Y is chlorine or hydrogen
Z is hydrogen or methyl In addition this invention relates to a method of increasing the yield of sugar obtained from sugarcane and more particularly to a method of increasing the recoverable sugar in sugarcane by treating the sugarcane during its maturation with these new compounds.

A variety of plant growth regulators, stimulants and promotors have been tried in the past in attempts to increase the yields of cultivated crops. It has been found that materials that have an effect on one crop will not necessarily have an effect or have a different effect on other crops.

One particular crop which has been given increased attention for the purpose of increasing yields is sugarcane. Accordingly it is an object of the present invention to provide new methods and compositions of increasing the yield of sugar obtained from sugarcane.

It has now been found that the recovery of sugar from sugarcane can be significantly increased by the use of certain esters. Consequently it has now been found that it is possible to increase the recoverable sugar in sugarcane by contacting the sugarcane plant with an effective amount of the aforedescribed compounds.

The compounds of the present invention can be prepared by reacting an acid chloride of the following structural formula:

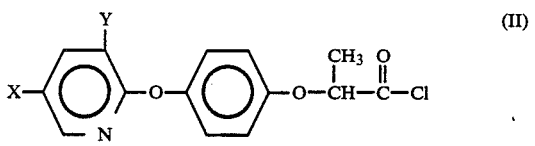

and an alcohol of the following structural formula:

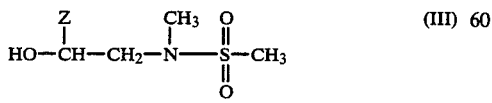

wherein
Z is as previously defined
in the presence of an acid scavenger as described in the following example.

EXAMPLE 1

Preparation of 1-(N-Methyl-Methanesulfonamido)-2-Propanol

N-Methylmethanesulfonamide (21.8 grams; 0.2 mol), t-butylalcohol (50 ml) sodium hydride (0.5 grams; 50% in mineral oil), and propylene oxide (11.6 grams; 0.2 mol) were placed into a 3-necked glass reaction flask equipped with stopper, stirrer, thermometer, and reflux condenser. The mixture was heated at 50°–60° C. for three hours, cooled, and concentrated on a roto-evaporator. The concentrate was neutralized with concentrated hydrochloric acid (1 ml) and distilled under reduced pressure. Fractions 4 and 5 (13.2 grams; boiling point (140°–142° C./1.5 mm Hg) analyzed for the described product as follows:

|  | Theoretical (%) | Found (%) |
|---|---|---|
| Carbon | 35.91 | 35.67 |
| Hydrogen | 7.84 | 7.90 |
| Nitrogen | 8.38 | 8.46 |
| Sulfur | 19.17 | 19.49 |

EXAMPLE 2

Preparation of 1-(N-methyl methanesulfonamido)-prop-2-yl 2-[4-(5-trifluoromethylpyridyl-2-oxy)phenoxy]-propionate 1-N-Methylmethanesulfonamido-2-propanol (40 grams; 0.024 mol), triethylamine (5 ml) and dichloromethane (150 ml) were placed into a 3-necked reaction flask equipped with stirrer. The mixture was cooled to 5° C. and 2-[4-(5-trifluoromethylpyridyl-2-oxy)-phenoxy]propionyl chloride (5.5 grams; 0.016 mol) in dichloromethane (30 ml) was added over a 5 minute period. The mixture was then stirred for 1 hour, washed once with water (50 ml), twice with potassium carbonate (50 ml; 10%) passed through phase separating paper and concentrated resulting in a red oil (6.5 grams). This concentrate was chromatographed through Florisil clay (150 ml) using hexane-ethyl acetate solvent. Fractions 8–10 yielded a yellow gum (1.2 grams) which was recrystallized from ethyl ether to give a white solid (0.4 grams), melting point 123°–125° C. Its infrared and elemental analysis were consistent with the desired product.

|  | Theoretical (%) | Found (%) |
|---|---|---|
| Carbon | 50.41 | 50.42 |
| Hydrogen | 4.85 | 4.87 |
| Nitrogen | 5.81 | 5.88 |
| Sulfur | 7.06 | 6.73 |

EXAMPLE 3

Preparation of 1-(N-Methyl methanesulfonamido)-prop-2-yl 2-[4-(5-chloropyridyl-2-oxy)phenoxy]propionate 1-N-Methyl-methanesulfonamido-2-propanol (1.6 grams; 0.0096 mol); toluene (80 ml) and triethylamine (5 ml) were placed into a 3-necked glass reaction flask equipped with stirrer, thermometer, addition funnel and nitrogen line. 2-[4(5-(Chloropyridyl-2-oxy)phenoxy]-propionyl chloride (2.87 grams; 0.0092 mol) in toluene solution was added to the mixture dropwise. Then the mixture was stirred at room temperature for an additonal 2.5 hours. At the end of this time period, the reaction mixture was transferred to a separatory funnel, washed four times with water (60 ml), dried through phase paper and stripped leaving a red/orange oil (3.5 grams). This oil was chromatographed through Florisil clay using hexane-ethyl acetate solvent. Fractions 9–13 were combined and analyzed for the desired product.

|  | Theoretical (%) | Found (%) |
| --- | --- | --- |
| Carbon | 51.52 | 49.94 |
| Hydrogen | 5.23 | 5.18 |
| Chlorine | 8.00 | 10.06 |
| Nitrogen | 6.33 | 5.97 |
| Sulfur | 7.24 | 6.79 |

EXAMPLE 4

Preparation of 2-(N-Methyl methanesulfonamido)-ethyl 2-[4-(5-chloropyridyl-2-oxy)phenoxy]propionate 2-N-Methylmethanesulfonamidoethanol (1.65 grams; 0.0107 mol); acetone (80 ml), toluene (30 ml), and triethylamine (5 ml) were placed into a 3-necked glass reaction flask equipped with stirrer, thermometer, addition funnel and nitrogen line. 2-[4-(5-Chloropyridyl-2-oxy)-phenoxy]propionyl chloride (3.18 grams; 0.0102 mol) in toluene solution was stirred into the mixture dropwise. Then the mixture was stirred at room temperature until the reaction was complete. It was then transferred to a round bottomed flask, stripped of acetone and toluene added. The mixture was washed in a separatory funnel four times with water (60 ml), dried through phase paper and stripped of solvent leaving an orange oily gum (4.5 grams). This product was chromatographed through Florisil clay (150 ml) with hexane-ethyl acetate solvent mixture. Fractions 7–10 were combined and analyzed for the desired product as follows:

|  | Theoretical (%) | Found (%) |
| --- | --- | --- |
| Carbon | 50.41 | 49.29 |
| Hydrogen | 4.94 | 4.89 |
| Chlorine | 8.27 | 9.54 |
| Nitrogen | 6.53 | 6.19 |
| Sulfur | 7.48 | 7.36 |

EXAMPLE 5

Preparation of 2-(N-Methylmethanesulfonamido)ethyl 2-[4-(3,5-dichloropyridyl-2-oxy)phenoxy]propionate 2-N-Methylmethanesulfonamidoethanol (1.65 grams; 0.0107 mol), acetone (30 ml) toluene (80 ml) and triethylamine (10 ml) were placed into a 3-neck glass reaction flask equipped with stirrer, thermometer, addition funnel and nitrogen line. 2-[4-(3,5-Dichloropyridyl-2-oxy)-phenoxy]propionyl chloride (3.46 grams; 0.01 mol) in toluene solution was stirred into the mixture dropwise. Then the mixture was stirred at room temperature until the reaction was complete, transferred to a round bottom flask, and stripped of acetone. Toluene was added, and the solution washed in a separatory funnel four times with water (60 ml). The product mixture was then dried through phase paper and stripped to leave an orange oil/gum (4.6 grams). This gum was chromatographed through Florisil clay (150 ml) and eluted with hexane-ethyl acetate solvent mixtures. Fractions 6–8 were consistent in infrared and elemental analysis with the desired product.

|  | Theoretical (%) | Found (%) |
| --- | --- | --- |
| Carbon | 46.66 | 45.42 |
| Hydrogen | 4.35 | 4.30 |
| Chlorine | 15.30 | 17.65 |
| Nitrogen | 6.05 | 5.74 |
| Sulfur | 6.92 | 6.51 |

EXAMPLE 6

Preparation of 1-(N-Methylmethanesulfonamidoprop-2-yl 2-[4-(3,5-Dichloropyridyl-2-oxy)phenoxy]propionate 1-N-Methylmethanesulfonamido-2-propanol (2.0 grams; 0.012 mol), triethylamine (3 ml) and acetone (100 ml) were placed into a glass reaction flask equipped with stirrer, dropping funnel, thermometer and reflux condenser and cooled to 5° C. 2-[4-(3,5-Dichloropyridyl-2-oxy)phenoxy]propionyl chloride (5.6 grams; 0.012 mol) in dichloromethane (20 ml) was added dropwise over a 5 minute period at 5°–10° C. This mixture was stirred for 1 hour, transferred to a round bottomed flask and stripped on a rotoevaporator. The concentrate was dissolved in toluene (100 ml), and washed with water (100 ml), twice with potassium carbonate solution (100 ml), and water (100 ml). It was dried through phase separating paper and concentrated leaving a product (3.6 grams) which was then chromatographed through Florisil clay using hexane-ethyl acetate solvent (150 ml). Fractions 3–6 analyzed for the desired product as follows:

|  | Theoretical % | Found % |
| --- | --- | --- |
| Carbon | 47.80 | 46.94 |
| Hydrogen | 4.65 | 4.74 |
| Chlorine | 14.85 | 16.19 |
| Nitrogen | 5.87 | 5.45 |
| Sulfur | 6.72 | 6.01 |

Infrared spectrum was consistent with structure.

EXAMPLE 7

Preparation of 2-(N-Methylmethanesulfonamido)ethyl 2-[4-(5-trifluoromethylpyridyl-2-oxy)phenoxy]propionate 2-N-Methylmethanesulfonamidoethanol (3.1 grams; 0.02 mol), triethylamine (5 ml) and dichloromethane (150 ml) were placed into a glass reaction flask equipped with a dropping funnel, stirrer, thermometer and nitrogen inlet tube. 2-[4-(5-Trifluoromethylpyridyl-2-oxy)-phenoxy]propionyl chloride (5.5 grams; 0.015 mol) dissolved in dichloromethane (30 ml) was added dropwise over a five minute period at 5°–10° C. The mixture was stirred at room temperature for 2 hours, transferred to a separatory funnel and washed twice with water (50 ml) and twice with potassium carbonate (50 ml).

It was then passed through phase separating paper and concentrated on a rotoevaporator leaving a red oil (6.5 grams). The oil was chromatographed through Florisil clay (150 ml) using hexane-ethyl acetate solvent and Fractions 10–12 analyzed for the desired product as follows:

|  | Theoretical (%) | Found (%) |
| --- | --- | --- |
| Carbon | 49.35 | 49.32 |
| Hydrogen | 4.58 | 4.61 |
| Nitrogen | 6.06 | 5.98 |
| Sulfur | 6.93 | 7.26 |

The effectiveness of the compounds of this invention for increasing the recoverable sugar in sugarcane is demonstrated by the following tests. The cane was harvested 8 weeks after application of the compound.

The top 14 joints of the treated cane as well as those of the controls were removed, combined and analyzed for juice purity and pol percent cane, following the "press method" developed and described by T. Tanimoto, Hawaiian Planters Record, 57, 133 (1964). Pol percent cane is a polarimetric determination and equals the percentage of sucrose if the latter is the only substance in the solution which will rotate the plane of polarized light. The pol percent cane is a standard method of determining the sucrose content of sugarcane.

|  | Rate of Application (lbs./acre) | Pol % Cane | Juice Purity |
| --- | --- | --- | --- |
| TEST 1 | | | |
| Compound of Example 2 | 1 | 13.00 | 82.87 |
| Control | 0 | 7.54 | 68.88 |
| TEST 2 | | | |
| Compound of Example 2 | 1 | 10.71 | 76.61 |
| Control | 0 | 8.54 | 69.31 |
| TEST 3 | | | |
| Compound of Example 2 | 1 | 14.53 | 88.71 |
|  | 0.5 | 13.07 | 86.18 |
|  | 0.1 | 13.49 | 87.60 |
| Control | 0 | 10.78 | 81.76 |

In the use of this compound to increase the recoverable sugar in sugarcane, sugarcane is treated at a late stage of development of the sugarcane wherein most of the sugar formation takes place. Thus, under normal growing conditions and common cultivation practices the active compound of this invention can be applied to the sugarcane during the period of from about 2 to about 10 weeks before harvesting.

The amount of active compound required to effectively increase the recoverable sugar from sugarcane can vary somewhat depending on such factors as the time of application, the weather, crop density, method of application and the like. Generally, an amount of at least 0.1 pounds per acre and preferably an amount of from 0.1 pounds per acre to about 10 pounds per acre can be used. While an amount greater than those mentioned can be used, they will not result in an advantage that would warrant their expense and are, therefore, not practical.

For practical use in treating sugarcane, the active compounds of this invention are generally incorporated into compositions or formulations which comprise an inert carrier and an effective amount of the compound. The compositions enable the active compound to be conveniently applied to the sugarcane at the desired rate. The formulations can be liquid formulations such as emulsifiable concentrates or solutions or solid formulations such as dusts, granules or wettable powders.

The preferred compositions are liquid formulations, particularly solutions or emulsifiable concentrates. Emulsifiable concentrates comprise the active compound, according to this invention, and as the inert carrier, a solvent and an emulsifier. Such emulsifiable concentrates can be extended with water and/or oil to any desired concentration of active compound for application as sprays to the sugarcane. The emulsifier most commonly used in these concentrates are nonionic or mixtures of nonionic with anionic surface-active agents. With the use of some emulsifier systems an inverted emulsion (water-in-oil) can be prepared.

Typical formulations according to the present invention useful for increasing the recoverable sugar in sugarcane are illustrated in the following examples wherein the quantities are given in parts by weight.

EXAMPLE 2

Preparation of an Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

Product of EXAMPLE 2: 25
Sodium lauryl sulfate: 2
Sodium lignin sulfate: 3
Kerosene: 70

EXAMPLE 3

Preparation of a Wettable Powder

The following components are mixed intimately in conventional mixing or blending equipment and are then ground to a powder having a particle size of less than about 50 microns. The finished powder is dispersed in water to give the desired concentration of active compound for application to the sugarcane.

Product of EXAMPLE 3: 50
Fuller's earth: 47
Sodium lauryl sulfate: 2.5
Methyl cellulose: 0.5

EXAMPLE 4

Preparation of a Dust

The following ingredients are mixed thoroughly and are then ground to an average particle size of less than about 50 microns to give a dust suitable for application with conventional dusting equipment.

Product of EXAMPLE 4: 10
Powdered talc: 90

The effectiveness of the compounds of this invention for increasing the recoverable sugar from sugarcane was demonstrated in a field test by applying a solution in acetone diluted for application to the various indicated application rates. The test compound was applied at each rate on the spindle area of each of 20 stalks of sugarcane in a field in Hawaii, using a syringe with a fine needle as the applicator. A set of 10 of these treated stalks from each group was harvested at 4 and 8 weeks after such treatment. In each harvest a set of 10 untreated stalks were also harvested as a control.

We claim:

1. A Compound of the formula:

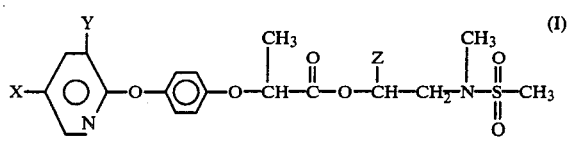

wherein

X is chlorine or trifluoromethyl

Y is chlorine or hydrogen

Z is methyl or hydrogen

2. The compound of claim 1, 1-(N-methylmethanesulfonamido)-prop-2-yl 2-[4-(5-trifluoromethylpyridyl-2-oxy)-phenoxy]propionate.

3. The compound of claim 1, 1-(N-methylmethanesulfonamido)-prop-2-yl 2-[4-(5-chloropyridyl-2-oxy)-phenoxy]propionate.

4. The compound of claim 1, 2-(N-methylmethanesulfonamido)-ethyl 2-[4-(3,5-dichloropyridyl-2-oxy)-phenoxy]propionate.

5. The compound of claim 1, 2-(N-methylmethanesulfonamido-ethyl 2-[4-(3,5-dichloropyridyl-2-oxy)-phenoxy]propionate.

6. The compound of claim 1, 1-(N-methylmethanesulfonamido)prop-2-yl 2-[4-(3,5-dichloropyridyl-2-oxy)-phenoxy]-propionate.

7. The compound of claim 1, 2-(N-methylmethanesulfonamido)ethyl 2-[4-(5-trifluoromethylpyridyl-2-oxy)-phenoxy]propionate.

8. A method for increasing the recoverable sugar contained in sugarcane which comprises contacting the sugarcane plant with an effective amount of a sulfonamide of claim 1.

9. The method of claim 8 wherein the sulfonamide is applied to the sugarcane plant at a rate of from about 0.1 to about 10 pounds per acre.

10. The method of claim 9 wherein the sulfonamide is applied to the sugarcane plants at the period from about 2 to about 10 weeks before harvest.

11. The method of claim 8, 9 or 10 wherein the sulfonamide is the compound of claim 2.

12. The method of claim 10 wherein the sulfonamide is the compound of claim 3.

13. The method of claim 10 wherein the sulfonamide is the compound of claim 4.

14. The method of claim 10 wherein the sulfonamide is the compound of claim 5.

15. The method of claim 10 wherein the sulfonamide is the compound of claim 6.

16. The method of claim 10 wherein the sulfonamide is the compound of claim 7.

* * * * *